United States Patent [19]

Tumer

[11] Patent Number: 5,446,288
[45] Date of Patent: Aug. 29, 1995

[54] INTEGRATED SUBSTANCE DETECTION INSTRUMENT

[76] Inventor: Tumay O. Tumer, 107 Sweetwood Ct., Riverside, Calif. 92506

[21] Appl. No.: 143,417

[22] Filed: Oct. 25, 1993

[51] Int. Cl.6 ................................. G01N 23/204
[52] U.S. Cl. ............................ 250/390.05; 250/392
[58] Field of Search ................ 250/390.05, 390.11, 250/392

[56] References Cited

U.S. PATENT DOCUMENTS

| | | |
|---|---|---|
| 4,300,054 | 11/1981 | Dance et al. . |
| 4,536,841 | 8/1985 | Waechter et al. . |
| 4,646,068 | 2/1987 | Skala ................................. 340/580 |
| 4,766,319 | 8/1988 | Regimand ..................... 250/390.05 |
| 4,864,142 | 9/1989 | Gomberg . |
| 4,935,194 | 6/1990 | Verschoore . |
| 5,083,019 | 1/1992 | Spangler . |
| 5,109,691 | 5/1992 | Corrigan et al. . |
| 5,135,704 | 8/1992 | Shefer et al. . |

FOREIGN PATENT DOCUMENTS 59-114446  7/1984  Japan ............................ 250/390.05

OTHER PUBLICATIONS

Hiroshi Tominaga, Nobuo Wada, Noboru Tachikawa, Yoshinori Kuramochi, Shoichi Horiuchi, Yoshihiro Sase, Hiro Amano, Naotake Okubo and Hiroshi Nishikawa, "Simultaneous Ulitlization of Neutrosn and γ-rays from $^{252}$Cf for Measurment of Moisutre and Density." *Int. J. Appl. Radiat. Isot.,* vol. 34, No. 1 (1983) pp. 429–436. [Copyright ⓡ 1983 Pergamon Press Ltd.
G. Sh. Pekarskii and N. V. Kilina, "A Neutron Method of Determining Water in Scrap Metal." Traslated from *Zavodskaya Laboratoriya,* vol. 42, No. 5 (May 1976) p 565. [Copyright ⓡ 1976 Plenum Publishing Corporation.

*Primary Examiner*—Constantine Hannaher
*Attorney, Agent, or Firm*—Townsend and Townsend Khourie and Crew

[57] ABSTRACT

A portable device used for non-destructive detection of illicit narcotics, or other hydrogen or light element containing substances, includes a weak, self-contained, radioactive source of fast neutrons and a detector for detecting scattered thermal neutrons and gamma rays. The detector design allows it to detect hermetically sealed or unsealed packages of narcotics or other materials concealed behind compartment barriers. The detector can also be used to detect the identity or type of material by simultaneously using both the gamma ray flux and thermal neutrons flux.

12 Claims, 4 Drawing Sheets

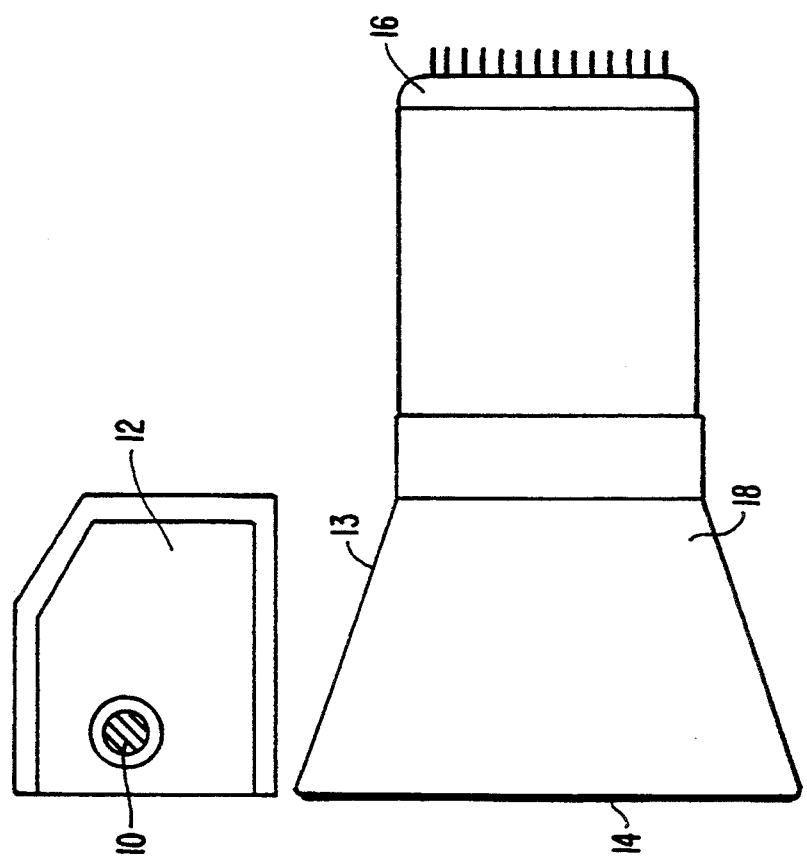
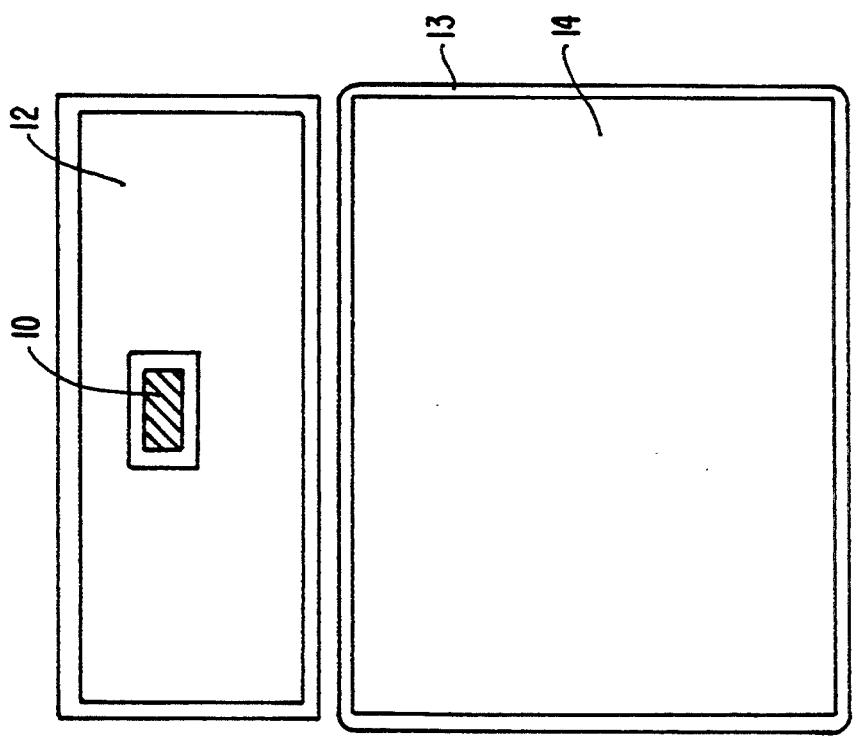

- RESPONSE TO 5 OZ. DRUGS (BORATED POLYETHYLENE)
- RESPONSE TO 5 OZ. DRUGS (PARAFFIN)

INTEGRATED SUBSTANCE DETECTION INSTRUMENT

BACKGROUND OF THE INVENTION

Narcotics use has been identified as one of the major social problems of the twentieth century. Governments have sought to reduce the traffic of narcotics by intensive searching of vessels used to transport narcotics between countries. However, such search and seizure tactics have not yet succeeded in reducing the level of narcotics use.

The major impediment to search and seizure operations is the concealment of narcotics in containers or structural parts of a vessel. Often these containers or structural parts are made of metal or some other rigid material. Thus, searching for narcotics requires destruction of personal property which requires strong justification.

Accordingly there is a need for non-destructively detecting narcotics or other substances concealed behind barriers of metal or other rigid materials. A portable, hand-held detector would be particularly useful to conduct quick, non-destructive searching of vessels at ports of entry.

Various techniques have been proposed to detect substances behind metal and other barriers. One such system is described in U.S. Pat. No. 4,864,142. That system utilizes the well-known phenomena of neutron resonance scattering, i.e., that a particular nuclei has large neutron cross sections for a neutron beam of a particular resonance energy characteristic of the particular nuclei. In that system, a tunable neutron source provides a beam of nuclei having the resonance energy of a nuclei desired to be detected. The source used is described in the patent at col. 10, lines 29–70, and utilizes a proton beam to generate neutrons. Since the protons are charge particles their energy can be controlled by passing the beam through a controllable potential difference.

The system disclosed in that patent can identify substances such as explosives or narcotics by detecting resonances indicating the presence of nuclei included in a substance to be detected. However, because of the requirement of tuning the energy of the neutron beam, the source requires electrical power and circuitry to control the potential difference applied to the proton beam. Thus, it would not be suited for use in a hand-held, portable device.

Other non-destructive search methods include the use of animals, sniffers, nuclear magnetic resonance, gamma ray scattering, and ultrasonics. Both animals and sniffers are unable to detect narcotics in hermetically sealed containers. Gamma rays and NMR are not effective to penetrate metal barriers. Ultrasonics is useful for probing liquid containers but not as effective otherwise.

SUMMARY OF THE INVENTION

The present invention is an apparatus and method for non-destructive searching for substances, such as narcotics, containing hydrogen or substances containing other light nuclei. A weak radioactive source is utilized to provide a flux of fast neutrons. A flux of thermal neutrons scattered from a substance containing hydrogen is detected to indicate the presence of the substance.

According to one aspect of the invention, the source is comprised of nuclei that undergo spontaneous fission to generate a fast neutron flux.

According to another aspect of the invention, the flux of fast neutrons is moderated to epithermal energies before being scattered by the substance to improve detection.

According to another aspect of the invention, the flux of epithermal neutrons is measured and the detector output is compensated to account for weakening of the source over time.

Other features and advantages of the invention will be apparent in view of the following detailed description and appended drawings.

BRIEF DESCRIPTION OF THE DRAWINGS

FIGS. 1A and 1B are block diagrams of the detector;

DETAILED DESCRIPTION OF THE PREFERRED EMBODIMENTS

1. Principle of Operation

Figure 2:
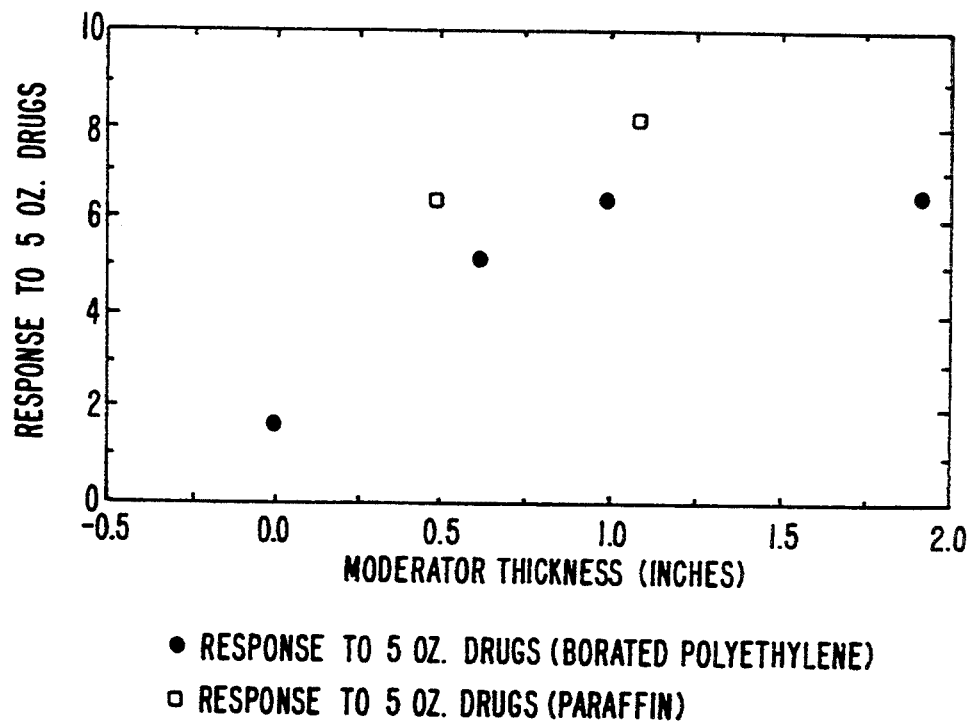
FIG. 2 is a graph depicting the dependence of the detector response on moderator thickness.

The present invention is based on the detection of the presence of hydrogen in a substance to be detected. Additionally, the detector can also be used to detect the presence of other light elements such as liquid He, Li, Be, and so forth. It is well-known that all narcotics contain significant amounts of hydrogen, as is illustrated in Table 1.

TABLE 1

| Generic Name | Chemical Composition | Chemical Formula | Hydrogen (%) | Carbon (%) | Oxygen (%) | Other |
|---|---|---|---|---|---|---|
| Marijuana | Cannabidiol | $C_{21}H_{31}O_2$ | 9.91 | 79.95 | 10.14 | |
| | Cannabinol | $C_{21}H_{26}O_2$ | 8.44 | 81.24 | 10.31 | |
| Cocaine | Cocaine | $C_{17}H_{21}NO_4$ | 6.98 | 67.31 | 21.10 | 4.62 |
| | Cocaine Hydrochloride | $C_{17}H_{22}ClNO_4$ | 6.53 | 60.08 | 18.83 | 14.55 |
| | Cocaine Nitrate | $C_{17}H_{22}NO_3$ | 6.05 | 55.73 | 30.57 | 7.65 |
| | Cocaine Sulfate | $C_{17}H_{22}NO_8S$ | 5.78 | 50.86 | 31.88 | 11.48 |
| Heroin | Diacetylmorphine | $C_{21}H_{23}NO_5$ | 6.28 | 68.28 | 21.66 | 3.79 |
| | Diacetyldihydromorphine | $C_{21}H_{25}NO_5$ | 6.28 | 68.28 | 21.66 | 3.79 |
| | Diacetylmor. Hydrochlor. | $C_{21}H_{24}ClNo_5$ | 5.96 | 62.14 | 19.71 | 12.19 |

Typically, it may be suspected that narcotics are hidden behind a barrier of metal or some other material, e.g., a bulkhead in a ship. It is desired to quickly detect the presence or absence without doing structural damage to the ship. In the present invention, an incident flux of fast neutrons (neutrons having an energy of several MeV) is directed toward the barrier and the presence of a flux of thermal neutrons (neutrons having an energy of less than 1 eV) is detected to indicate the presence of a hydrogen containing substance behind the barrier.

The ability to penetrate the metal barrier is due to the fact that very little energy is transferred from the neutrons in the incident flux to the nuclei in the metal because the nuclei are much more massive than the neutron. By analogy, if the neutron were a marble and the nuclei were a billiard ball the marble would bounce off the billiard ball at almost its initial velocity. Thus, there is a low probability that the neutron would collide with enough metal nuclei to reduce its energy to the thermal level.

However, hydrogen nuclei have about the same mass as neutrons and most of the energy of a neutron is transferred in a small number of collisions. By analogy, if both the neutron and the nuclei were marbles, a large part of the marble's velocity would be transferred to the other marble in each collision. The number of collisions required to reduce a fast neutron to thermal energy for various initial energies and nuclei are set forth in Table 2.

TABLE 2

| Incident Neutron Energy | Hydrogen | Carbon | Iron | Lead |
|---|---|---|---|---|
| 1 MeV | 17.5 | 110.8 | 490 | 1820 |
| 5 MeV | 19.1 | 120.9 | 535 | 1988 |
| 25 MeV | 20.7 | 131.9 | 580 | 2159 |

A major advantage of this detection system is that the incident neutron flux does not need to be tuned to a particular energy. Thus, a self-contained, sealed radioactive source that requires no power supply can be utilized. Of special significance is the fact that the required intensity of the incident neutron flux is so low that special nuclear safety procedures are not necessary.

2. System Overview

FIGS. 1A and 1B are schematic top and side views, respectively, of a preferred embodiment of the invention. In the figures a self-contained, radioactive source of fast neutrons 10 is enclosed by a moderator 12. A detector 13 includes a scintillator 14 coupled to a photomultiplier tube (PMT) 16 by an air light guide 18. Alternatively, a photo-diode or avalanche photo-diode can be substituted for the PMT 16.

The radioactive source 10 generates an incident flux of fast neutrons having an energy determined by the specific material utilized as the source. The moderator 12 is utilized to lower the energy of the incident neutron flux to optimize the detection efficiency. The moderator 12 also reduces the amount of radiation emitted from the back of the detector thereby increasing the safety of the device. The source and moderator are described more fully below.

Generally, a scintillator generates a flash of light when the energy of an incident nuclear particle or gamma ray is absorbed. The flash of light is converted to an electrical pulse by the PMT or photo-diode. In the preferred embodiment, the scintillator 14 is designed to have negligible response to fast neutrons and gamma rays emitted from the source 10 and to have a high response to thermal neutrons scattered from a hydrogen containing substance. Additionally, PMT threshold voltage levels and pulse discrimination techniques may be utilized to reduce the response to gamma rays thereby improving signal to noise ratios.

The magnitude of the detected flux of thermal neutrons is indicated by a counts/second value on a display, by a speaker or headphone output indicating counts/second, or by an LED display including several LEDs selectively activated to indicate the signal level.

3. Description of Neutron Source and Moderator

The radioactive source of fast neutrons is either an isotope that undergoes spontaneous fission or a source that undergoes nuclear reactions where the incident particle is the result of a conventional decay process.

Many transuranic heavy nuclides have appreciable spontaneous fission decay probabilities. Several fast neutrons are emitted promptly in each fission event. Therefore, a small amount of such a radionuclide can be a simple and convenient isotopic neutron source. Because fission sources emit many other products, encapsulation in source containers sufficiently thick so that only fast neutrons and gamma rays emerge is required. Encapsulation also facilitates passing Nuclear Regulatory Commission (NRC) licensing requirements.

A common fission source is $Cf^{252}$ having a half-life of 2.65 years which is long enough for practical applications. It is used as a source of fast neutrons in the preferred embodiment because of its low average neutron energy of about 2 MeV. A 0.1 microgram sample of $Cf^{252}$ has been utilized as the source.

An alternative self-contained source comprises an alpha-emitting isotope with a suitable target material that emits neutrons when bombarded with alpha particles. Other sources such as $Am^{241}Be$ could be utilized but would cause difficulties in passing NRC licensing requirements.

The moderator is fabricated from a material, such a polyethylene or paraffin, that is known to slow down neutrons. The thickness of the moderator is varied to optimize detector efficiency. FIG. 2 is a graph displaying the response as a function of moderator material and thickness for a particular case.

4. Description of Neutron Detector

The most critical component of the thermal neutron detector 13 is the scintillator 14. As described above, the source 10 emits fast neutrons and gamma rays. Since the source 10 and the detector 13 are close to each other the detector 13 will be subject to a continuous flux of fast neutrons and gamma rays from the source 10. Excellent discrimination against fast neutrons and gamma rays is essential.

A $^6Li$ based detector is utilized in the preferred embodiment. The required discrimination is achieved by selecting a detection material sufficiently thick to stop thermal neutrons and reaction products but thin enough that the fast neutrons pass through without appreciable interactions. Additionally, thin detectors such as a 0.5 mm thick $^6Li$—Sn(Ag) plastic scintillator do not show a peak for thermal neutrons. Therefore, careful setting of the discriminator threshold is required. Also, the pulse shapes for neutrons and gamma rays are significantly different and pulse shape discrimination can be utilized to reduce signal to noise ratios.

$^6Li$ based detectors are based on the $^6Li(n,alpha)$ reaction. As is well known in the art, other scintillation materials based on either the $^{10}B(n,alpha)$ or the $^3He(n,p)$ reaction can be utilized to detect slow neutrons. Gamma rays are also normally detected by the scintillator but can be discriminated from neutrons because the generated pulses have different heights and shapes than neutrons.

5. System Electronics and Implementation

Figure 3:
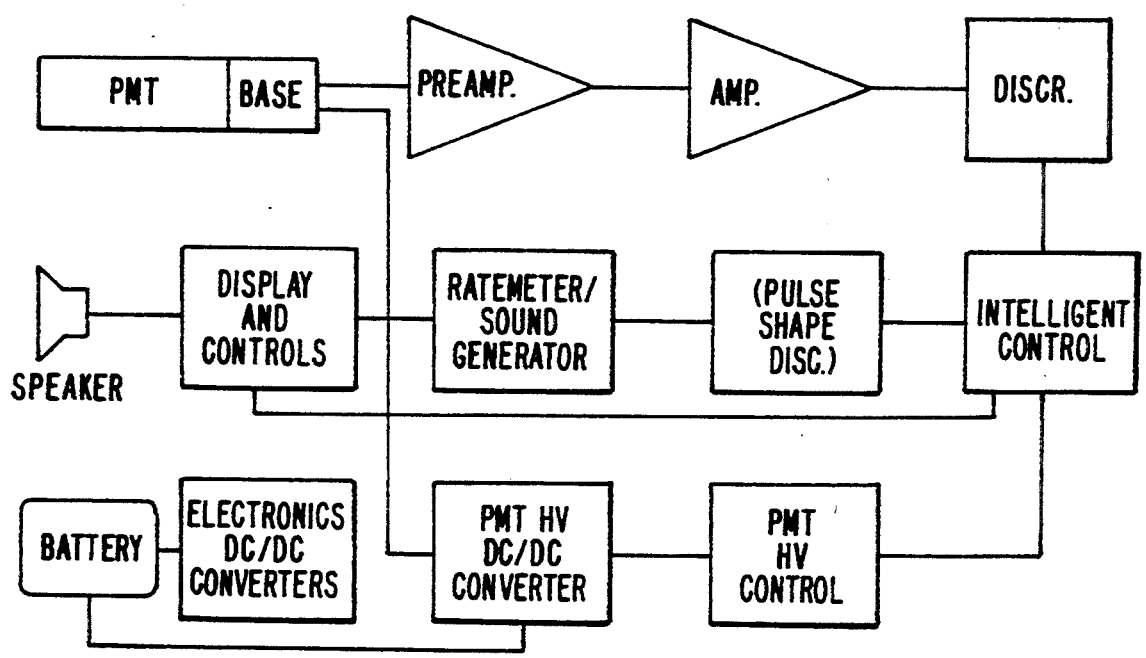
FIG. 3 is a block diagram of the detector electronics.

A block diagram of the detector electronics is depicted in FIG. 3. The circuit includes preamplifier, amplifier (possibly with pulse shaping), discriminator, intelligent control, rate meter, display, and operator control. A microcomputer is utilized to provide the intelligent control. Pulse discrimination can be utilized to optimize the signal to noise ratio for $^6$Li based detectors. Battery and DC/DC convertors for the electronics power supply and PMT high voltage power supplies can be located inside the detector.

The intelligent control also can implement a background mode. First, a count/rate is established for a background reading. Then, during normal operation the background count reading is subtracted from the actual count rate being detected.

6. Physical Realization Including Sound, Headphone, and LED Outputs.

Figure 4A:
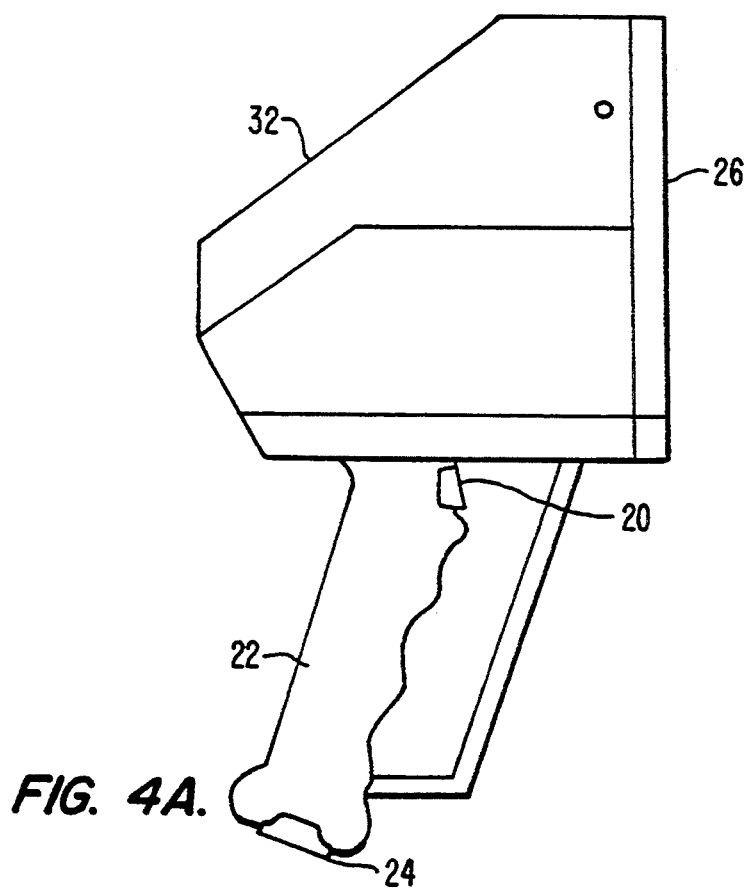
FIGS. 4A, 4B, and 4C are depictions of a physical embodiment of the invention.
Figure 4B:
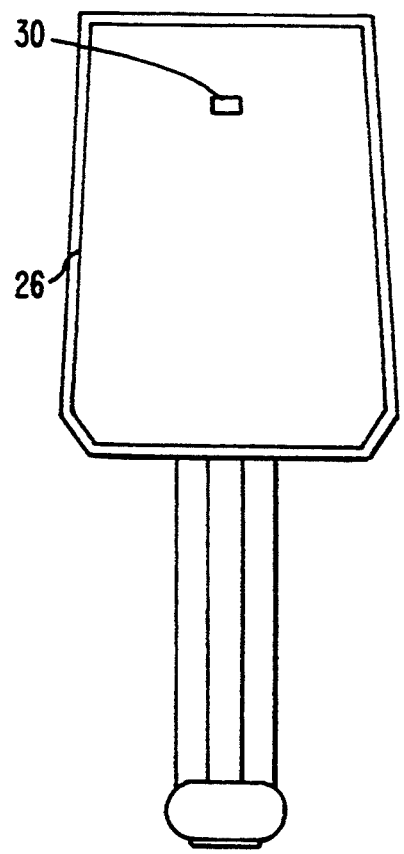

FIGS. 4A, B, and C are side, front, and back views, respectively, of a physical embodiment of a narcotics detector implementing some of the principles of the invention. A trigger 20 functions as the on/off switch. A handle 22 functions as a battery compartment with a battery cap 24 disposed at the bottom of the handle. The front face 26 of the case 28 includes an opening 30 exposing the source of fast neutrons. A back face 32 of the case 28 includes the control and display panel 34.

Figure 4C:
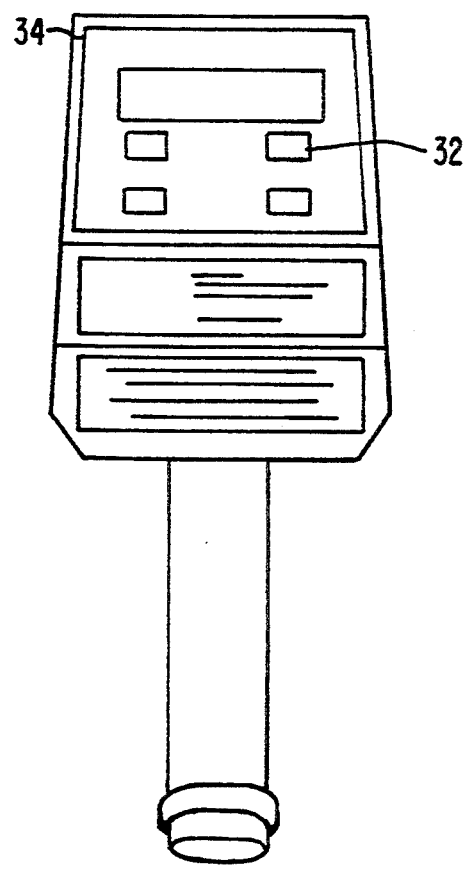
Figure 5:
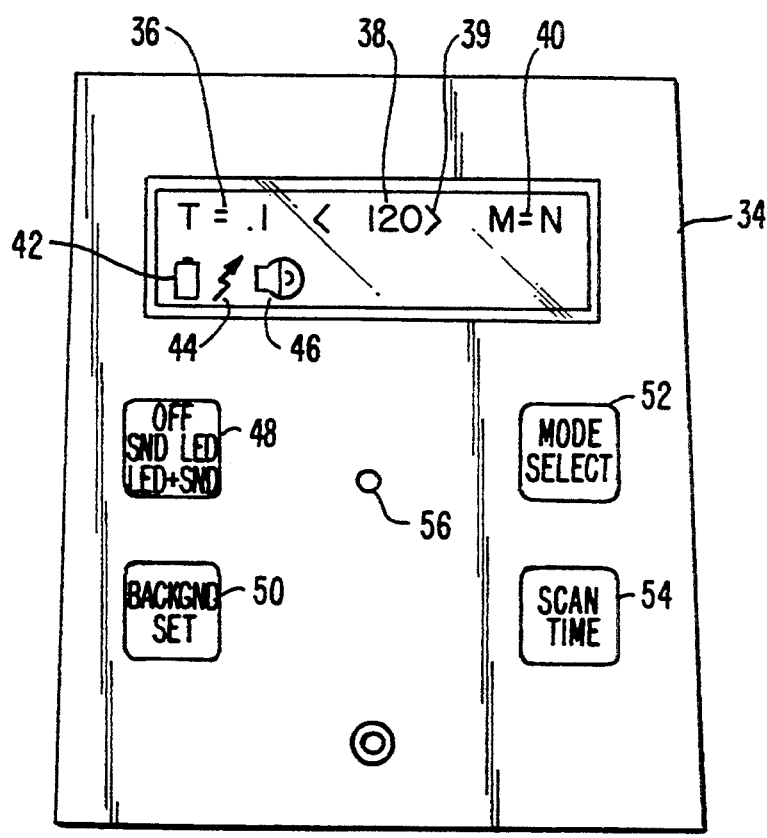
FIG. 5 is depiction of the control panel and displays.

FIG. 5 depicts the control and display panel 34 of FIG. 4C. An LCD displays the scan time 36, the count rate 38, the display lock indicator 39, a display mode indicator 40, a low battery mode indicator 42, an LED on indicator 44, and sound on indicator 46. The control panel includes a SOUND/LED on/off switch 48, BACKGROUND SET switch 50, MODE SELECT switch 52, and SCAN TIME set switch 54. An LED 56 display includes four LEDs of different colors which indicate the magnitude of the detected flux of thermal neutrons.

7. Examples of Scan Techniques

Prior to conducting a search the detector is initialized by pointing it in the air. A scan time can be set through the operator controls. Less sensitive scans can be done using faster integration times such as 0.1 or 0.3 seconds while more sensitive scans can be done using 1 or 3 seconds. A default mode of 1 second is provided in the preferred embodiments.

At this point a background count is always present due to either natural radiation sources or from the source of epithermal neutrons. In the preferred mode the background rate can either be ignored (Normal Mode) or compensated (Background Mode) by subtracting it from the signal.

When using the background mode it is important to reset the background whenever locations are changed, e.g., moving to a different panel or container. Further, it is advisable to reset the background from time to time because environmental conditions may have changed.

To set the background count rate the front face of the detector is placed onto a part of the panel surface which is known to be "clean" or free of narcotics The BACKGROUND SET button is pushed and the detector is held still for about 15 seconds to obtain background data.

In both modes the search procedure is the same, the front face is placed on the surface of a panel or a container. The detector is then slid over up and down to search for a change in the output signal. A typical scan may have visual and audio outputs activated. A change in the output signals may indicate something under the panel to raise suspicions about that location. A scan initiated from a different point on the surface could be used to verify the suspicion.

User knowledge is helpful to decide whether it is probable that narcotics are located at the suspicious location. For example, count rates for different substances have been supplied and others should be tabulated to give an indication of the nature the substance behind the panel. Further, knowledge of the structure of the container is useful. For example, sometimes a rubber seal will be detected. This can be confirmed by running the detector around the edge of the container to determine if the signal changes. It is the change of signal which is significant. An operator will soon gain enough experience either to temper or pique suspicion.

8. Material Identification by Using Both the Observed Gamma Ray and Neutron Signals The gamma ray signal backscattered from the target substance is separated from the neutron signal and can also be observed. Gamma rays mainly scatter from electrons in a material and thermal neutrons scatter from the nuclei of hydrogen and other light elements. Therefore, the gamma ray signal measures electron density and neutron signal indicates the presence of hydrogen and other light elements and the signals are complementary.

During a scan of a substance these two signals could be used to determine the identity or type of the material observed. One way to determine the type of material would be to plot the gamma ray and neutron count rates in a computer memory and from the intercept, slope and shape of these points (curves) determine the identity or type material or substance observed.

The invention has now been described with reference to the preferred embodiments. Alternatives and substitutions that fall within the scope of the invention will now be apparent to persons of skill in the art. For example, various types of sources of fast neutrons may be utilized as well as a variety of detectors of thermal neutrons. Additionally, alternative ways of indicating the count rate to a user can be substituted. Accordingly, it is not intended to limit the invention except as provided by the appended claims.

What is claimed is:

1. A portable system for detecting hydrogen or other light element containing substances comprising:
    a weak radioactive source for providing a flux of fast neutrons;
    a detector for detecting a scattered flux of thermal neutrons and for generating a detector output signal indicating the magnitude of said scattered flux;
    an output device, coupled to said detector, for converting said detector output signal to a format indicating the magnitude of said scattered flux to a user;
    a case for enclosing said source and detector and for supporting said output device, wherein said case has a front face and said detector is oriented to detect a flux of thermal neutrons incident upon said front face; and
    a moderator, disposed between said source and said front face, for transforming said flux of fast neutrons to a flux of epithermal energy neutrons.

2. The system of claim 1 further comprising:
a calibration circuit for measuring the magnitude of the flux provided by said source and adjusting the detector output signal to account for a decrease of said flux over time due to radioactive decay.

3. The system of claim 1 wherein said output device comprises:
means for indicating the number of thermal neutrons detected per unit of time.

4. The system of claim 1 further comprising:
means for subtracting a background count from air and a barrier from said detector output signal to compensate said signal.

5. A method for detecting hydrogen or other light element containing substances disposed behind a barrier having a front, said method comprising the steps of:
providing a weak radioactive source for providing a flux of fast neutrons and a detector for detecting a scattered flux of thermal neutrons and generating a detector output signal indicating the magnitude of said scattered flux;
positioning the source at a first position on the front side of the barrier;
moderating said flux of fast neutrons to epithermal energy to improve detection;
positioning the detector near said source; and
comparing the magnitude of said detector output signal to a predetermined magnitude to determine whether a hydrogen or light element containing substance is disposed behind said barrier in the vicinity of said first position.

6. The method of claim 5 further comprising the step of:
enclosing said source and detector in a portable, hand-held case.

7. The method of claim 5 further comprising:
measuring the intensity of the flux provided by said source prior to positioning the source; and
compensating said detector output signal to account for decrease in the intensity of the flux provided by said source due to the reduction of activity of said source over time.

8. The method of claim 5 further comprising:
measuring the intensity of flux scattered only from air and said barrier to form a background signal; and
subtracting said background signal from said detector output signal to determine the magnitude of the neutron flux scattered from said hydrogen or light element containing substance.

9. A portable system for detecting hydrogen or other light element containing substances comprising:
a weak radioactive source for providing a flux of fast neutrons;
a detector for detecting a scattered flux of thermal neutrons and for generating a detector output signal indicating the magnitude of said scattered flux;
means for moderating the energy levels of said fast neutrons to optimize the sensitivity of said detector;
an output device, coupled to said detector, for converting said detector output signal to a format indicating the magnitude of said scattered flux to a user; and
a case for enclosing said source and detector and for supporting said output device, wherein said case has a front face and said detector is oriented to detect a flux of thermal neutrons incident upon said front face.

10. A portable system for detecting hydrogen or other light element containing substances comprising:
a weak radioactive source for providing a flux of fast neutrons;
a detector for detecting a scattered flux of thermal neutrons and for generating a detector output signal indicating the magnitude of said scattered flux;
means for subtracting a background count from air and a barrier from said detector output signal to compensate said signal;
an output device, coupled to said detector, for converting said detector output signal to a format indicating the magnitude of said scattered flux to a user;
a case for enclosing said source and detector and for supporting said output device, wherein said case has a front face and said detector is oriented to detect a flux of thermal neutrons incident upon said front face; and
a moderator, disposed between said source and said front face, for transforming said flux of fast neutrons to a flux of epithermal energy neutrons.

11. A portable system for detecting hydrogen or other light element containing substances comprising:
a weak radioactive source for providing a flux of fast neutrons;
a detector for detecting a scattered flux of thermal neutrons and for generating a detector output signal indicating the magnitude of said scattered flux;
an output device, coupled to said detector, for converting said detector output signal to a format indicating the magnitude of said scattered flux to a user;
a case for enclosing said source and detector and for supporting said output device, wherein said case has a front face and said detector is oriented to detect a flux of thermal neutrons incident upon said front face; and
a moderator, surrounding said source, for transforming said flux of fast neutrons to a flux of epithermal energy neutrons.

12. A portable system for detecting hydrogen or other light element containing substances comprising:
a weak radioactive source for providing a flux of fast neutrons;
a detector for detecting a scattered flux of thermal neutrons and for generating a detector output signal indicating the magnitude of said scattered flux;
an output device, coupled to said detector, for converting said detector output signal to a format indicating the magnitude of said scattered flux to a user;
a case for enclosing said source and detector and for supporting said output device, wherein said case has a front face and said detector is oriented to detect a flux of thermal neutrons incident upon said front face; and
a moderator in proximity of said source for transforming said flux of fast neutrons to a flux of epithermal energy neutrons.

* * * * *

UNITED STATES PATENT AND TRADEMARK OFFICE
CERTIFICATE OF CORRECTION

PATENT NO. : 5,446,288
DATED : August 29, 1995
INVENTOR(S) : Tümay O. Tümer

It is certified that error appears in the above-identified patent and that said Letters Patent is hereby corrected as shown below:

At column 1, line 4, insert the following:

-- GOVERNMENT RIGHTS NOTICE

This invention was made with U.S. Government support under Contract Number DTRS-57-91-C-00004, awarded by the Department of Transportation. The U.S. Government has certain rights in the invention.--

Signed and Sealed this

Sixth Day of October, 1998

Attest:

BRUCE LEHMAN

Attesting Officer

Commissioner of Patents and Trademarks